(12) United States Patent
Al-Harthi et al.

(10) Patent No.: US 9,346,938 B1
(45) Date of Patent: May 24, 2016

(54) POLY(ACRYLIC ACID)-GLYCEROL BLENDS

(71) Applicant: King Fahd University of Petroleum and Minerals, Dhahran (SA)

(72) Inventors: Mamdouh Ahmed Al-Harthi, Dhahran (SA); Osamah Awadh Bin-Dahman, Dhahran (SA); Sadhan Kumar De, Kolkata (IN); Jobin Jose, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 14/718,525

(22) Filed: May 21, 2015

(51) Int. Cl.
| | |
|---|---|
| *C08F 20/06* | (2006.01) |
| *C08L 33/02* | (2006.01) |
| *C08K 5/053* | (2006.01) |
| *B29C 39/00* | (2006.01) |
| *B29K 35/00* | (2006.01) |
| *B29L 7/00* | (2006.01) |
| *A61L 15/20* | (2006.01) |
| *C08F 6/10* | (2006.01) |
| *A61F 13/53* | (2006.01) |
| *A61L 15/24* | (2006.01) |

(52) U.S. Cl.
CPC ............... *C08K 5/053* (2013.01); *B29C 39/003* (2013.01); *A61F 2013/530481* (2013.01); *A61L 15/20* (2013.01); *A61L 15/24* (2013.01); *B29K 2035/00* (2013.01); *B29K 2995/0077* (2013.01); *B29L 2007/00* (2013.01); *C08F 6/10* (2013.01); *C08F 20/06* (2013.01); *C08L 33/02* (2013.01); *C08L 2666/34* (2013.01)

(58) Field of Classification Search
CPC ...... C08F 20/06; C08L 33/02; C08L 2666/34; C08K 5/053
See application file for complete search history.

(56) References Cited

U.S. PATENT DOCUMENTS

| 4,861,539 A * | 8/1989 | Allen ...................... A61L 15/60 264/204 |
| 2004/0022755 A1* | 2/2004 | Kamath ............... A61K 9/2072 424/70.16 |
| 2005/0153123 A1* | 7/2005 | Herfert ............. A61F 13/15203 428/327 |

FOREIGN PATENT DOCUMENTS

| CN | 104059192 A | 9/2014 |
| GB | 1491272 | 11/1977 |
| JP | 61-12883 | 4/1986 |

* cited by examiner

*Primary Examiner* — Richard A Huhn
(74) *Attorney, Agent, or Firm* — Oblon, McClelland, Maier & Neustadt, L.L.P

(57) ABSTRACT

Poly(acrylic acid) polymer blends comprising poly(acrylic acid) and glycerol, the glycerol content being 25-75% by weight based on the weight of the poly(acrylic acid). The polymer blends are miscible; they retain the ability to absorb large volumes of liquids and also exhibit rubber viscoelasticity. The incorporation of glycerol reduces the glass transition temperature of the blends dramatically. The process of preparing the poly(acrylic acid) polymer blends by solution casting is described. Methods of measuring the glass transition temperature and the tensile strength of the polymer blends are also provided.

9 Claims, 1 Drawing Sheet

POLY(ACRYLIC ACID)-GLYCEROL BLENDS

BACKGROUND OF THE INVENTION

1. Technical Field

The present invention relates to poly(acrylic acid) polymer blends. More particularly, The present invention relates to blends of poly(acrylic acid) and glycerol with fluid-absorbent and elasticity properties that are prepared by a solution casting process. These polymer blends are especially suitable for applications such as but not limited to biomedical applications and personal disposable hygiene products.

2. Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Poly(acrylic acid) (PAA), which is also known as carbomer, is one of the most significant water soluble polymers and forms the base of a class of materials termed 'super absorbent polymers' because of its ability to absorb water many times of its original volume and also its capability to retain water under pressure. As a result of these unique features, PAA is widely used in applications such as controlled release devices, membranes, disposable diapers, ion exchange resins, tissue engineering, toothpastes and so on J. Jose, F. Shehzad, and M. A. Al-Harthi, "Preparation method and physical, mechanical, thermal characterization of poly (vinyl alcohol)/poly(acrylic acid) blends," *Polym. Bull.*, July 2014—incorporated herein by reference in its entirety]. The swelling performance of PAA can be controlled by crosslinking reaction and copolymerization or via preparing composites by incorporating suitable nanofillers through solution polymerization [J. Lin, J. Wu, Z. Yang, and M. Pu, "Synthesis and Properties of Poly(acrylic acid)/Mica Superabsorbent Nanocomposite," *Macromol. Rapid Commun.*, vol. 22, no. 6, pp. 422-424, March 2001; A. Li, A. Wang, and J. Chen, "Studies on poly(acrylic acid)/attapulgite superabsorbent composite. I. Synthesis and characterization," *J. Appl. Polym. Sci.*, vol. 92, no. 3, pp. 1596-1603, May 2004; Z.-Q. Zhu, H.-X. Sun, X.-J. Qin, L. Jiang, C.-J. Pei, L. Wang, Y.-Q. Zeng, S.-H. Wen, P.-Q. La, A. Li, and W.-Q. Deng, "Preparation of poly(acrylic acid)-graphite oxide superabsorbent nanocomposites," *J. Mater. Chem.*, vol. 22, no. 11, p. 4811, February 2012—each incorporated herein in its entirety]. Blends of PAA with poly(vinyl alcohol) (PVA) and with poly (2-hydroxyethyl vinyl ether) (PHEVE) prepared by solution mixing and casting process show high degree of miscibility with an increase in storage modulus with temperature [W. Herrera-Kao and M. Aguilar-Vega, "Storage modulus changes with temperature in poly(vinyl alcohol), PVA,/poly(acrylic acid), PAA, blends," *Polym. Bull.*, vol. 42, no. 4, pp. 449-456, May 1999; V. V. Khutoryanskiy, M. G. Cascone, L. Lazzeri, N. Barbani, Z. S. Nurkeeva, G. a. Mun, A. B. Bitekenova, and A. B. Dzhusupbekova, "Hydrophilic Films Based on Blends of Poly(acrylic acid) and Poly(2-hydroxyethyl vinyl ether): Thermal, Mechanical, and Morphological Characterization," *Macromol. Biosci.*, vol. 3, no. 2, pp. 117-122, February 2003—each incorporated herein by reference in its entirety]. Also, the addition of PAA to PVA caused a considerable reduction in crystallinity and the prepared blends showed sensitivity to pH changes during swelling test [N. A. Peppas and D. Tennenhouse, "Semicrystalline poly (vinyl alcohol) films and their blends with poly (acrylic acid) and poly (ethylene glycol) for drug delivery applications," *J. Drug Deliv. Sci. Technol.*, vol. 14, no. 4, pp. 291-297, 2004—incorporated herein by reference in its entirety]. The subsequent thermal treatment leads to the formation of cross-linking between PAA with methyl cellulose polymer and the prepared material has ability to swell in water and ethanol [V. V Khutoryanskiy, M. G. Cascone, L. Lazzeri, Z. S. Nurkeeva, G. A. Mun, and R. A. Mangazbaeva, "Phase behaviour of methylcellulose-poly (acrylic acid) blends and preparation of related hydrophilic films," *Polym. Int.*, vol. 52, no. 1, pp. 62-67, January 2003—incorporated herein by reference in its entirety]. Recently, it was found that the developed blends of PAA and poly(ethylene glycol) are potential material for thermal energy storage applications at their miscibility conditions [C. Alkan, E. Gunther, S. Hiebler, and M. Himpel, "Complexing blends of polyacrylic acid-polyethylene glycol and poly(ethylene-co-acrylic acid)-polyethylene glycol as shape stabilized phase change materials," *Energy Convers. Manag.*, vol. 64, pp. 364-370, December 2012—incorporated herein by reference in its entirety].

BRIEF SUMMARY OF THE INVENTION

According to one aspect, the present invention relates to a poly(acrylic acid) polymer blend comprising poly(acrylic acid) and glycerol. The poly(acrylic acid) polymer blend prepared by a process comprising dissolving the poly(acrylic acid) and the glycerol in ethanol at a glycerol/poly(acrylic acid) weight ratio of 1:4 to 3:4 to form a polymer solution, pouring the polymer solution into a casting mold and drying the polymer solution in the casting mold to form the poly (acrylic acid) polymer blend.

In one or more embodiments, the glycerol crosslinks the poly(acrylic acid) by hydrogen bonds and without covalent bonds.

In one or more embodiments, the poly(acrylic acid) and the glycerol in the poly(acrylic acid) polymer blend are miscible in one another.

In one or more embodiments, the poly(acrylic acid) polymer blend has a glass transition temperature of no higher than 50° C.

In one or more embodiments, the poly(acrylic acid) polymer blend has a glass transition temperature of 20-30° C.

In one or more embodiments, the poly(acrylic acid) has a concentration of 15-20 g/L in the polymer solution.

In one or more embodiments, the glycerol/poly(acrylic acid) weight ratio is 2:5 to 3:5.

In one or more embodiments, the mixing is carried out at room temperature for 45-50 hours.

In one or more embodiments, the polymer solution is dried at room temperature for 3-7 days then at 45-60° C. for another 3-7 days.

In one or more embodiments, the poly(acrylic acid) polymer blend has an elongation at break of 200% or higher.

In one or more embodiments, the poly(acrylic acid) polymer blend has an elongation at break of 200-300%.

In one or more embodiments, the poly(acrylic acid) polymer blend has an ultimate tensile strength of 1-10 MPa.

In one or more embodiments, the poly(acrylic acid) polymer blend has an ultimate tensile strength of 1-5 MPa.

In one or more embodiments, the poly(acrylic acid) polymer blend has a tensile modulus of 10-50 MPa.

In one or more embodiments, the poly(acrylic acid) polymer blend has a tensile modulus of 20-30 MPa.

In one or more embodiments, the poly(acrylic acid) polymer blend comprises 30-60% glycerol based on the total weight of the poly(acrylic acid) polymer blend.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
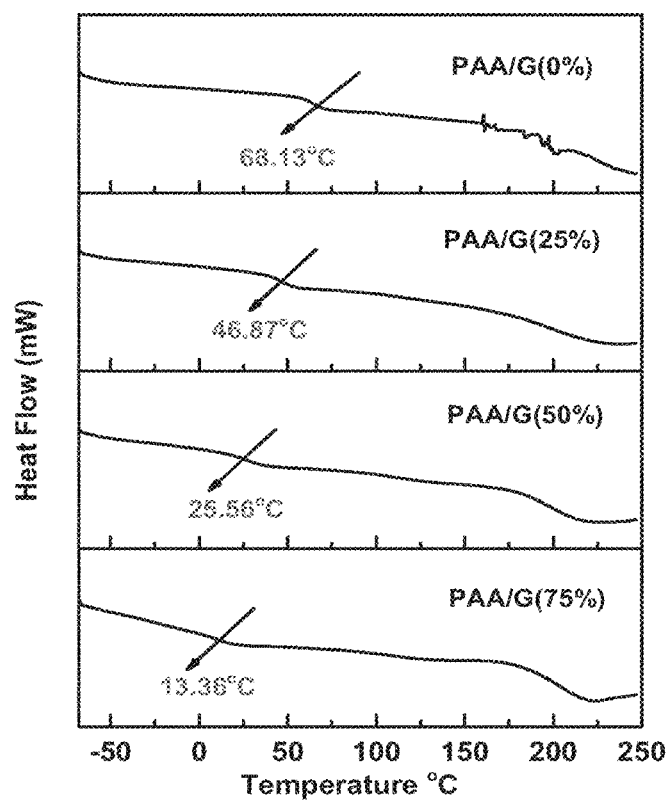
FIG. 1 shows the DSC analysis results of the second heating cycle.

Referring now to the drawings, wherein like reference numerals designate identical or corresponding parts throughout the several views.

The present invention provides novel poly(acrylic acid) or PAA polymer blends and a process for producing the same. Glycerol is physically crosslinked with PAA at different proportions to form the PAA-glycerol blends having rubber-like elasticity in addition to the excellent fluid-absorbent or hygroscopic characteristic that PAA is known for.

For purposes of the invention, the terms "polymer blend", "polymer mixture" or simply "blend" refer to a mixture of two or more polymers which can be homogeneous (miscible polymer blend), heterogeneous and having separate phases (immiscible polymer blend or sometimes called polymer alloy) or immiscible but exhibiting macroscopically uniform physical properties (compatible polymer blend). The PAA-glycerol blends provided herein are miscible polymer blends where the glycerol molecules form hydrogen bonds (physical crosslinks) to join two adjacent PAA chains with two of the three hydroxyl groups on the glycerol molecule. Contrary to chemical crosslinking, physical crosslinking does not involve covalent interactions between the crosslinking agent and the polymer chains and can therefore be readily reversed or reformed, for example, by heat (thermal degradation) or microbial activity (biodegradation).

The glycerol content in the PAA-glycerol blends are varied from 5-80% by weight based on the weight of the poly(acrylic acid), preferably 10-75%, more preferably 20-75%, even more preferably 25-75% or a glycerol/PAA ratio by weight of 1:4 to 3:4, most preferably 40-60%. In one embodiment, a PAA-glycerol blend has a glycerol content of 25%. In another embodiment, the glycerol content of a PAA-glycerol blend is 50%. In yet another embodiment, the glycerol content is 75%.

The addition of glycerol to PAA proportionally reduces the glass transition temperature ($T_g$) of PAA, thereby resulting in the formation of the polymer blends that retain their viscoelasticity at ambient or room temperature (16-26° C. or with an average of 20-22° C.). As used herein, the term "glass transition temperature" ($T_g$) refers to a temperature range, at which amorphous materials such as polymers transition between a hard, brittle, glassy state to a molten, rubbery state. $T_g$ is usually expressed as a singular value when the transition between the glassy state and the rubbery state reaches 100%. When the polymer is cooled below the $T_g$, it becomes hard and rigid. Above the $T_g$, the mobility of the polymer chains increase significantly and the polymer assumes a more pliable nature. PAA has a glass transition temperature about 70° C. and exists as a glassy material at room temperature, The PAA-glycerol blends described herein have a glass transition temperature, as measured by differential scanning calorimetry (DSC), of no higher than 50° C., preferably 10-50° C., more preferably 15-48° C., even more preferably 15-35° C., more preferably 20-30° C. In at least one embodiment, the DSC $T_g$ measurements are carried out according to the ASTM E1356 Standard Test Method for Assignment of the Glass Transition Temperature for Differential Scanning calorimetry, which is incorporated herein by reference in its entirety. Further to the glass transition temperature, the PAA-glycerol blends can be characterized based on their tensile strength, for example, in a tension test by the strip test method and/or the grab test method, and by various parameters including but not limited to elongation at break, ultimate tensile strength and tensile modulus. The strip test method determines the tensile strength, break failure of force and extension characteristics of a sample for a given rate of displacement. On the other hand, the grab test method determines the tensile strength only, of force and extension characteristics of a sample for a given rate of displacement. In some embodiments, the tension test is in accordance with at least one of the following ASTM methods: the ASTM D412 Standard Test Methods for Vulcanized Rubber and Thermoplastic Elastomers-Tension, the ASTM D638 Standard Test Method for Tensile Properties of Plastics, the ASTM D1456 Standard Test Method for Rubber Property—Elongation at Specific Stress and the ASTM Standard Test Method for Young's Modulus, tangent Modulus, and Chord Modulus, all of which are incorporated herein by reference in their entireties.

Accordingly, the PAA-glycerol blends have an elongation at break of at least 200%, preferably 200-300%, more preferably 225-300%, even more preferably 250-300%. As used herein, the term "elongation at break" refers to the maximum strain that can be placed on a material before it breaks or ruptures. The ultimate tensile strength of these blends is up to 10 MPa, preferably 1-10 MPa, more preferably 1-5 MPa, even more preferably 2-4 MPa. The terms "ultimate tensile strength", "tensile strength" and "ultimate strength" refer to the maximum stress that a material can withstand while being stretched or pulled before failing or breaking. The measured tensile modulus, which is also known as Young's modulus is 10-50 MPa, preferably 15-35 MPa, more preferably 20-30 MPa, yet more preferably 25-30 MPa. The terms "tensile modulus", "Young's modulus" and "elastic modulus" refer to a measure of the stiffness of an elastic material defined as the ratio of the stress (force per nit area) along an axis to the strain (ratio of deformation over initial length). Comparatively, natural rubber has an elongation at break of 450-700%, an ultimate tensile strength of about 16 MPa and a tensile modulus of 10-100 MPa.

The molecular weight of the PAA (glycerol units not inclusive) ranges from 100,000-2,000,000, preferably 500,000-1,500,000, more preferably 1,000,000-1,500,000. In one embodiment, the PAA has a molecular weight of 1,250,000. As the PAA and glycerol are forming physical crosslinking, the glycerol crosslinking units do not affect the molecular weight of resulting PAA blend.

The process by which the PAA-glycerol blends can be prepared is simple and cost-effective. Adopting a polymer solution casting technique and without involving any chemical polymerization of monomers, the entire manufacturing process may take place at atmospheric pressure and at room temperature. Dry poly(acrylic acid) or carbomer resin is initially dissolved in an organic solvent at a concentration of 15-20 g/L at room temperature. Examples of the organic solvent include but are not limited to ethanol, isopropanol, benzene and toluene. In one embodiment, the organic solvent is ethanol. The PAA resin should not contain any crosslinker that is commonly used in commercially prepared carbomer resins such as allyl ether pentaerythritol, allyl ether of sucrose or allyl ether of propylene. Dry non-crosslinked PAA is available as pure PAA powder or as a sodium or potassium salt, if acquired commercially. In some embodiments, the PAA starting material exists as a stock solution (with PAA only) or a salt solution and is therefore diluted to the desired concentration of 15-20 g/L in the organic solvent.

Glycerol is then added to the PAA solution. The amount of glycerol added is as previously defined herein. The PAA-glycerol mixture solution is then degassed and kept stirring at 500-600 rpm at room temperature for at least 24 h and up to 72 h, preferably 36-60 h, more preferably 40-50 h. In one embodiment, the PAA-glycerol mixture solution is stirred for 48 h. The stirred PAA-glycerol mixture is then poured into a casting mold, laid on a leveled flat surface and allowed to dry at room temperature for 3-7 days and then at 45-60° C. for another 3-7 days. At the end of the drying, the produced PAA-glycerol blend is non-adhesive and can be detached as whole from the mold without breakage. The dried PAA-glycerol polymer blend comprises 20-80% by weight of glycerol based on the total weight of the polymer blend, preferably 30-60%, more preferably 40-50%.

In some embodiments, the PAA-glycerol blend can be combined with additives such as plasticizers (for increased plasticity or fluidity), inorganic and organic fillers (for reinforcement), and stabilizers. Examples of plasticizers include but are not limited to diisononyl phthalate, diallyl phthalate, di-2-ethylhexyl-phthalate, dioctyl phthalate and diisodecyl phthalate (phthalate esters). Examples of fillers include but are not limited to oxides (e.g. MgO, $SiO_2$, $Sb_2O_3$, $Al_2O_3$, ZnO); hydroxides (e.g. $Al(OH)_3$, $Mg(OH)_2$); salts (e.g. $CaCO_3$, $BaSO_4$, $CaSO_4$, phosphates, hydrotalcite); silicates (e.g. talc, mica, kaolin, wallostonite, montmorillonite, feldspar, asbestos); metals (e.g. boron, steel); carbon and graphite (e.g. carbon fibers, graphite fibers, carbon nanotubes, carbon black); natural polymers (e.g. cellulose fibers, wood flour and fibers, flax, cotton, sisal, starch); and synthetic polymers (e.g. polyamide, polyester, aramid, polyvinyl alcohol fibers). Examples of stabilizers include but are not limited to antioxidants (e.g. hindered phenols, secondary aromatic amines, benzofuranones); hindered amine light stabilizers; UV absorbers (e.g. oxanilides, benzophenones, benzotriazoles, hydroxyphenyltriazines); antiozonants; and organosulfur compounds.

The following examples further illustrate the protocols and techniques used in the preparation of the PAA-glycerol polymer blends and the characterization of the blends. These examples are not intended to limit the scope of the appended claims.

EXAMPLE 1

Preparation of the Poly(Acrylic Acid) Glycerol Blends

Blends of poly(acrylic acid) (PAA) and glycerol were prepared by means of solution casting method. First of all, 4 g of PAA was dissolved in ethanol (250 ml) at room temperature under stirring at 600 rpm. After the PAA had dissolved completely, glycerol was added based on the formulations as shown in Table 1. Then the polymer mixture was degassed for 15 min to remove any traces of air from the solution. After that, the solution was kept under stirring at 600 rpm at room temperature for two days. Finally, the polymer mixture was poured into a plastic plate placed on a leveled flat surface and allowed to dry at room temperature for one week and then in an air oven at 50° C. also for another week.

TABLE 1

Formulations used in preparing the PAA/G blends

| Sample Code | Amount of Glycerol, g |
|---|---|
| PAA/G(0%) | 0.0 |
| PAA/G(25%) | 1.0 |
| PAA/G(50%) | 2.0 |
| PAA/G(75%) | 3 |

Poly(acrylic acid) is a glassy material at room temperature. The incorporation of glycerol into PAA reduces the glass transition temperature of PAA proportionally. The blends become softer and softer with an increase in glycerol content. Three types of PAA-glycerol blend samples were produced herein. The first type of samples with little or small amount of glycerol showed brittle character and the sample could not be taken out as whole from the plastic plate after the complete drying. On the other hand, the blends with very high amount of glycerol to that of PAA produced very soft and sticky samples. The sample with 50% of glycerol (by weight per weight of PAA) produced a rubbery material with excellent handling property.

EXAMPLE 2

Differential Scanning Calorimetry (DSC) Analysis of PAA-Glycerol Blends

The thermal behavior of the blends was determined by using DSC-Q1000, Universal V4.2E TA Instruments under Nitrogen atmosphere at a heating rate of 10° C./min. The DSC thermogram was taken in two heating cycles. The first heating cycle was from room temperature to 100° C. to remove any traces of moisture present in the sample which is likely to occur in a PAA polymer. The second heating cycle was done in the temperature region of −70° C. to 250° C. Calibrations in DSC were done by measuring the temperature and the enthalpy of melting of indium.

FIG. 1 displays the DSC analysis results of PAA/G samples. It can be seen that the addition of glycerol led to a dramatic decrease in the glass transition temperature of PAA, i.e. from 68.13° C. (PAA) to 46.87° C. (PAA+25% glycerol) to 25.56° C. (PAA+50% glycerol) to 13.36° C. (PAA+75% glycerol).

EXAMPLE 3

Tensile Tests of PAA-Glycerol Blends

In order to study the rubbery nature or mechanical properties of the prepared PAA-glycerol blends, a tension test was performed on the PAA-glycerol blend with 50% glycerol (PAA/G (50%)). The tension test was performed using a Universal Testing Machine (INSTRON 3366). The test was conducted at a crosshead speed of 10 mm/min and the load cell was 1 kN. The sample gauge length was kept as 20 mm. The sample was cut into a strip of 5 mm width and the average thickness was measured as 0.55 mm thickness.

Figure 2:
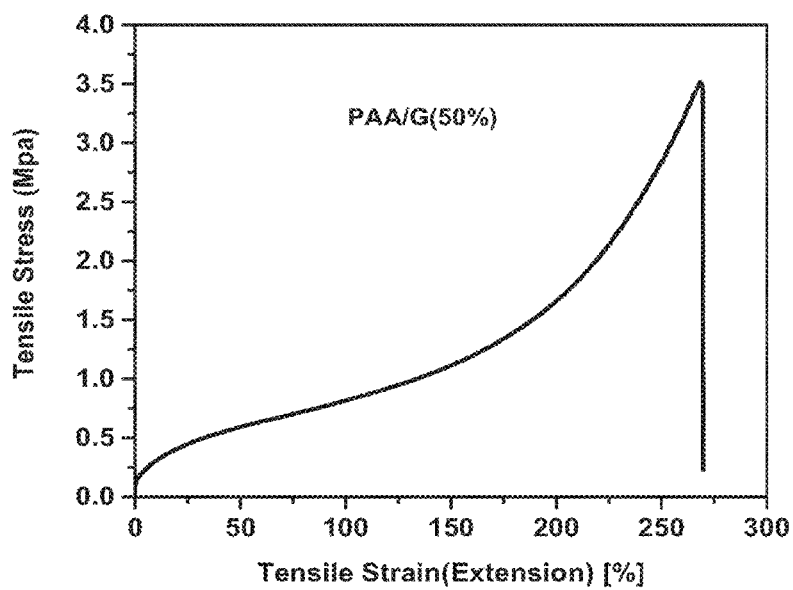
FIG. 2 shows the tensile stress-strain curve of PAA/G (50%) sample.

FIG. 2 shows the stress-strain curve of the PAA/G (50%) sample. The elongation at break was 269%, ultimate tensile strength (UTS) was 3.58 MPa and tensile modulus was 26.25 MPa.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. An article comprising:
    a poly(acrylic acid) polymer blend consisting of poly(acrylic acid and glycerol, wherein the glycerol crosslinks the poly(acrylic acid) by forming hydrogen bonds and no covalent bonds to join two adjacent poly(acrylic acid) chains, and wherein the poly(acrylic acid) polymer blend is prepared by a process comprising:
    mixing the poly(acrylic acid) in an organic solvent to form a poly(acrylic acid) solution;
    adding and mixing glycerol to the poly(acrylic acid) solution at a glycerol/poly(acrylic acid) weight ratio of 1:4 to 3:4 to form a blended polymer solution; and
    pouring the blended polymer solution into a casting mold and drying to form the poly(acrylic acid) polymer blend;
    wherein the article is a disposable hygiene product.

2. The article of claim 1, wherein the poly(acrylic acid) and the glycerol in the poly(acrylic acid) polymer blend are miscible in one another.

3. The article of claim 1, wherein the poly(acrylic acid) polymer blend has a glass transition temperature of no higher than 50° C.

4. The article of claim 1, wherein the poly(acrylic acid) polymer blend has a glass transition temperature of 20-30° C.

5. The article of claim 1, wherein the glycerol forms the hydrogen bonds to join the two adjacent poly(acrylic acid) molecules with two of three hydroxyl groups on a glycerol molecule.

6. The article of claim 1, wherein the glycerol is added to the poly(acrylic acid) solution at a glycerol/poly(acrylic acid) weight ratio of 1:2.

7. The article of claim 1, wherein the poly(acrylic acid) solution has a concentration of 15-20 g of the poly(acrylic acid) per liter of the organic solvent.

8. The article of claim 1, wherein the organic solvent is selected from the group consisting of ethanol, isopropanol, benzene and toluene.

9. The article of claim 1, wherein the adding and mixing of the glycerol to the poly(acrylic acid) solution is carried out at room temperature for 45-50 hours.

* * * * *